United States Patent [19]

Brock et al.

[11] 4,041,203

[45] Aug. 9, 1977

[54] NONWOVEN THERMOPLASTIC FABRIC

[75] Inventors: Robert J. Brock, Neenah; Gary H. Meitner, Winneconne, both of Wis.

[73] Assignee: Kimberly-Clark Corporation, Neenah, Wis.

[21] Appl. No.: 729,356

[22] Filed: Oct. 4, 1976

Related U.S. Application Data

[63] Continuation-in-part of Ser. No. 460,363, April 12, 1974, abandoned, which is a continuation-in-part of Ser. No. 286,691, Sept. 6, 1972, abandoned.

[51] Int. Cl.² .................................... B32B 27/00
[52] U.S. Cl. .................................... 428/157; 156/291; 428/212; 428/220; 428/286; 428/296; 428/298; 428/300; 428/302; 428/340; 428/903; 428/910
[58] Field of Search .............. 428/195, 198, 286, 288, 428/296, 297, 298, 302, 332, 515, 903, 910; 156/219, 220, 291, 309

[56] References Cited

U.S. PATENT DOCUMENTS

| | | | |
|---|---|---|---|
| 3,016,599 | 1/1962 | Perry | 428/338 |
| 3,341,394 | 9/1967 | Kinney | 428/292 |
| 3,676,242 | 7/1972 | Prentice | 156/62.4 |
| 3,704,198 | 11/1972 | Prentice | 428/198 |
| 3,755,527 | 8/1973 | Keller et al. | 264/210 F |
| 3,795,571 | 3/1974 | Prentice | 428/296 |
| 3,837,995 | 9/1974 | Floden | 428/296 |
| 3,849,241 | 11/1974 | Butin et al. | 428/137 |

Primary Examiner — James J. Bell
Attorney, Agent, or Firm — Leydig, Voit, Osann, Mayer & Holt, Ltd.

[57] ABSTRACT

A non-woven fabric-like material comprising an integrated mat of generally discontinuous, thermoplastic polymeric microfibers and a web of substantially continuous and randomly deposited, molecularly oriented filaments of a thermoplastic polymer. The polymeric microfibers have an average fiber diameter of up to about 10 microns while the average diameter of filaments in the continuous filament web is in excess of about 12 microns. Attachment between the microfiber mat and continuous filament web is achieved at intermittent discrete regions in a manner so as to integrate the continuous filament web into an effective load bearing constituent of the material. The material has desirable strength characteristics and possesses a textile-like appearance, drape and hand. By autogenously bonding the mat and web together in a manner so as to provide substantially uniform discrete bond regions, particularly outstanding strength characteristics with respect to energy absorption, tensile strength, and tear resistance can be achieved.

26 Claims, 4 Drawing Figures

NONWOVEN THERMOPLASTIC FABRIC

This application is a continuation-in-part of our copending application Ser. No. 460,363 filed Apr. 12, 1974, which in turn, is a continuation-in-part of our earlier copending application Ser. No. 286,691, filed Sept. 6, 1972, both of which are now abandoned.

The present invention relates generally to nonwoven fabrics and, more particularly, to nonwoven fabrics composed predominantly of synthetic, thermoplastic fibers with desirable fabric-like characteristics, and to method of manufacturing such fabrics.

It is a primary object of the present invention to provide a nonwoven material of synthetic thermoplastic fibers which is strong and yet has a textile-like drapability and which is uniformly opaque thus presenting a cloth-like appearance.

A further object of the present invention resides in providing a material having the above-described characteristics which also possesses a full bodied hand without being clingy and which has a comfortable, moist feel without being clammy.

A still further object is to provide a nonwoven material embodying the above-discussed features which is sufficiently breathable so as to be useful in garment related applications and yet possesses desirable water repellent characteristics. Closely related to this object is the additional object of providing such a material which can be independently treated by simple and conventional means to impart characteristics so as to render the material water absorbent.

Yet another object is to provide a material as above described possessing desirable surface abrasion characteristics.

An additional objective is to provide a nonwoven material which is simple and inexpensive to manufacture and which is useful in a wide spectra of applications such as garments, wipes, and the like.

A specific object resides in providing a material having many of the previously identified attributes which can be advantageously used as a wrapper or containment fabric for surgical or other health care procedures.

Additional objects and advantages of the present invention will become apparent upon reading the following detailed description of the invention taken in conjunction with the attached drawings in which.

While the invention will be described in connection with preferred embodiments, it is to be understood that the invention is not to be limited to those embodiments. On the contrary, all alternatives, modifications, and equivalents as can be included within the scope and spirit of the invention defind in the appended claims are intended to be covered.

Figure 1:
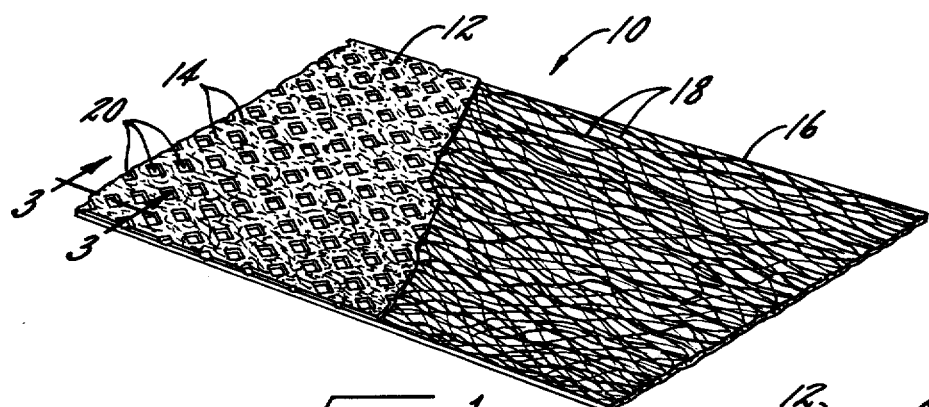
FIG. 1 is a schematic fragmentary perspective view, with sections thereof broken away, of a material embodying the features of the present invention.

Turning now to the drawings, FIG. 1 depicts a nonwoven material 10 in the form of a laminate having as a top layer an integrated mat 12 of generally discontinuous, thermoplastic microfibers 14 and, as a bottom layer, a web 16 of substantially continuous and randomly deposited, molecularly oriented filaments 18 of a thermoplastic polymer. As illustrated, in order to provide a unitary structure, ply attachment between the mat and web is effected at the intermittent discrete bond regions 20 which are disposed over the surface of the material in a substantially regular pattern. While as hereinafter discussed, it is preferred that the discrete bond regions 20 be formed by the application of heat and pressure at the illustrated intermittent areas, other methods of ply attachment such as the use of independently applied adhesives or mechanical interlocking of the fibers such as by needling techniques or the like can also be used.

The integrated mat 12 of thermoplastic polymeric microfibers can be prepared by known techniques such as is set forth in an article entitled "Superfine Thermoplastic Fibers" appearing in INDUSTRIAL & ENGINEERING CHEMISTRY, Vol. 48, No. 8, pp. 1342-1346 which describes work done at the Naval Research Laboratories in Washington, D.C. Also, see Naval Research Laboratoy Report 111437, dated Apr. 15, 1954, U.S. Pat. Nos. 3,715,251, 3,704,198, 3,676,242 and 3,595,245, and British Specification No. 1,217,892. Basically, the method of formation involves extruding a molten polymeric material into fine streams and attenuating the streams by opposing flows of high velocity, heated gas (usually air) to break the streams into discontinuous fibers of small diameter. Subsequent collection of the fibers on a foraminous screen belt, drum or the like yields a mat of the microfibers. The mat posseses integrity due to entanglement of the individual fibers in the mat as well as some degree of thermal or self-bonding between the fibers, particularly when collection is effected only a short distance after extrusion. In general, the microfibers contained in such mats have an average fiber diameter of up to about only 10 microns with very few, if any, of the fibers exceeding 10 microns in diameter. Usually, the average diameter of the fibers in such mats is about 2-6 microns. While the fibers in the mat are predominantly discontinuous, they generally have a length exceeding that normally associated with staple fibers.

Turning now to the web 16 of substantially continuous filaments, the manner of preparing this web is also customary with illustrative techniques being set forth in the followin patents: Kinney (U.S. Pat. Nos. 3,338,992 and 3,341,394); Levy (U.S. Pat. No. 3,276,944); Peterson (U.S. Pat. No. 3,502,538); Hartmann (U.S. Pat. Nos. 3,502,763 and 3,509,009); Dobo et al. (U.S. Pat. No. 3,542,615); and Harmon (Canadian Pat. No. 803,714).

While many different methods are illustrated for initially preparing such continuous filament webs, the available methods generally have at least three common features. First, the methods of preparation involve continuously extruding a thermoplastic polymer (either from the melt or a solution) through a spinneret in order to form discrete filaments. Thereafter, the filaments are drawn (either mechanically or pneumatically) without breaking in order to molecularly orient the polymer filaments and achieve tenacity. Lastly, the continuous filaments are deposited in a substantially random manner onto a carrier belt or the like to form a web of substantially continuous and randomly arranged, molecularly oriented filaments. A preferred method for preparing such webs is described in U.S. patent application, Ser. No. 865,128, filed Oct. 9, 1969, now U.S. Pat. No. 3,692,618.

As opposed to the above-discussed microfiber web, the continuous filaments 18 in the web 16 generally have an average fiber diameter in excess of about 12 microns and up to about 55 microns. For use herein, webs containing continuous filaments with an average diameter of about 15–25 microns are preferred. In addition, due to molecualr orientation of the filaments, their tenacity is considerably higher than that of the microfibers in the mat 12.

As is apparent, the preparation of the constituents of the nonwoven material depicted in FIG. 1 is simple and inexpensive, involving conventional extrusion, melt blowing and spinning techniques. Basically, the only raw material required for the preparation of the illustrated nonwoven material is a thermoplastic polymer Moreover, it will be appreciated that the simple addition of a pigment to the polymer prior to extrusion permits inexpensive preparation of colored fabrics without the necessity for post-dying operations which are often difficult and expensive to accomplish.

Regarding the polymers used in preparing the illustrated microfiber mat and continuous filament web, a wide variety of thermoplastic polymers are useful. The mat and web can be prepared from the same or different polymer types and two or more different polymers can be used in the preparation of either the mat or web or both. Thus, materials embodying the features of the present invention can be fashioned with different physical properties by the appropriate selection of polymers or combinations thereof for the respective mat and web. Among the many useful thermoplastic polymers, polyoleinfs such as polypropylene and polyethylene, polyamides, polyesters such as polyethylene teraphthalate, and thermoplastic elastomers such as polyurethanes are anticipated to find the most wide spread use in the preparation of the materials described herein.

In further keeping with the present invention, nonwoven materials can be prepared as illustrated herein with a wide variety of weights, with the particular weight of a given material being selected on the basis of the intended end use application. For most uses, the total weight of the material will not ordinarily exceed about 4 oz./yd.$^2$ with materials in the weight range of about 0.75–2.5 oz./yd.$^2$ generally being most useful for fabric-type applications. Where particularly high strength is required in the resultant material, the microfiber mat should be included in a lesser weight amount than the continuous filament web. However, useful material embodying the features of the present invention can generally be prepared with the weight ratio of mat to web being about 0.2:1 to 4:1.

Figure 2:
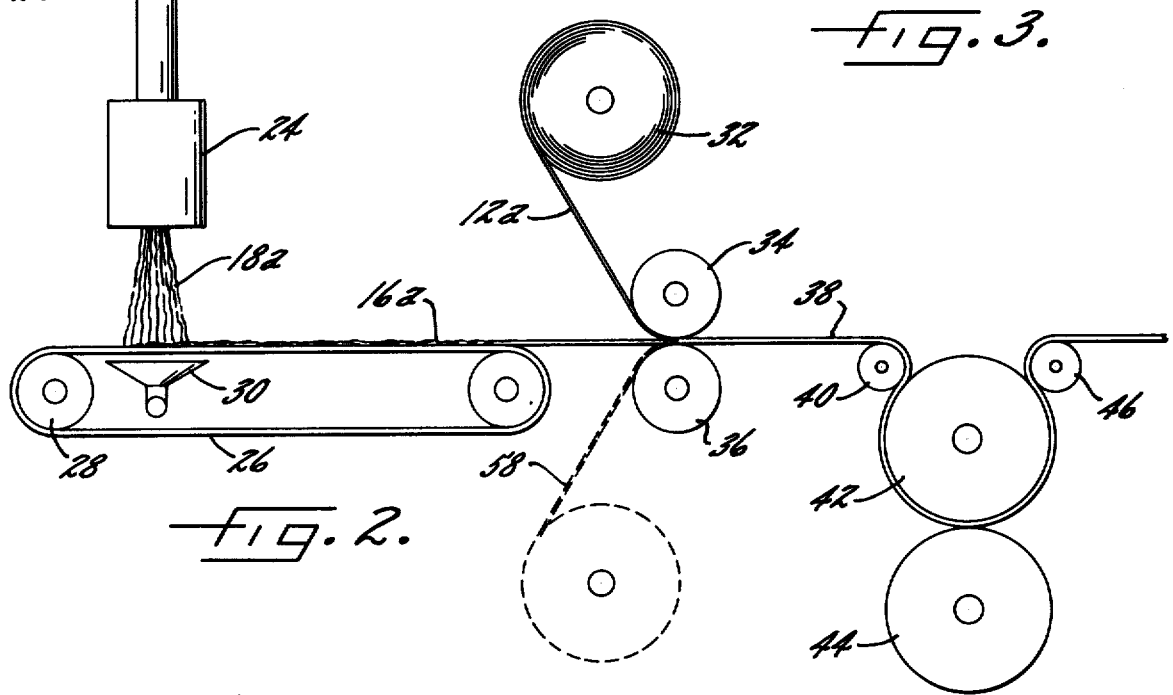
FIG. 2 is a schematic side elevation view illustrating one manner in which the material of the present invention can be prepared.

Turning now to FIG. 2, there is illustrated one manner of continuously preparing a nonwoven material such as depicted in FIG. 1 wherein corresponding elements are correspondingly numbered with the addition of the subscript a. As shown, preparation of the continuous filament web 16a is effected by introducing polymer into the extruder 22 and thereafter extruding the polymer in the form of filaments through a spinneret (not shown), drawing the spun filaments by means of the take off device schematically illustrated at 24 and thereafter depositing the drawn continuous filaments 18a in a substantially random manner onto the moving foraminous carrier belt 26 driven over the roll 28 in the form of the web 16. Appropriate suction means 30 can be present to assist in web formation on the carrier belt 26.

As formed on the belt 26, the web 16a is substantially unbonded and is very tenuous and weak. In addition, while the filaments 18a are substantially randomly arranged to form the web 16a, as a practical matter complete randomness is rarely accomplished and, as a result, the web 16a is not completely uniform in appearance which detracts from its suitability as such in fabric-like applications.

Referring still to FIG. 2, after preparation of the continuous filament web 16a the preformed, integrated microfiber mat 12a unwound from the roll 32 is brought into laminar contact with the web 16a at the nip between the rolls 34, 36 to form the unbonded two ply laminate 38. Thereafter, ply attachment between the mat 12a and web 16a is effected by passing the unbonded laminate 38 over the idler roll 40 and into contact with the heated smooth surfaced roll 42 and subsequently through the pressure nip formed between the heated roll 42 and the heated roll 44 which contains a plurality of raised points on its surface in the pattern generally illustrated in FIG. 1. The bonded laminate is then removed from the roll 42 over the idler roll 46.

In order to prepare a nonwoven fabric in the manner illustrated in FIG. 2 which possesses the combination of desirable strength characteristics and textile-like drapability, it is necessary that the web of substantially continuous filaments be integrated into an effective load bearing constituent without an accompanying adverse effect on the drapability. To this end, it is important that the bonding conditions (temperature, pressure, and to a lesser degree, dwell time in the nip) as well as the pattern of bonding be appropriately selected. Concerning the bond pattern, an intermittent bond pattern is preferably employed with the pattern being substantially regularly repeating over the surface of the web. The pattern of the raised points on the roll 44 is selected such that the area of the web occupied by the bonds after passage through the nip is about 5–50% of the surface area of the material with the discrete bonds being present in about 50–1000/in.$^2$. Preferably, the bonds occupy about 10–30% of the surface area and are present in a density of about 100–500/in.$^2$.

Regarding the bonding conditions, it will be appreciated that bonding must have the two-fold effect of achieving ply attachment between the mat and web and of integrating the continuous filament web into a coherent, strong constituent so that the resulting material has desirable strength characteristics. It is believed that the illustrated construction containing a microfiber mat in laminar contact with a continuous filament web allows the mirofiber mat to function in this two-fold capacity when the thermoplastic polymer of the mat is a polymer with a slightly lower softening point than the polymer of the web.

In general, the softening point of the polymer in the microfiber mat, or a portion thereof, should be at least about 10° C. less than the softening point of the web polymer and not more than about 40° C., and preferably 35° C., lower. If the mat polymer softens at a temperature appreciably below the web polymer, it is difficult to achieve appropriate bonding without an accompanying adverse film forming effect on the surface of the microfiber mat. Differential Thermal Analysis (DTA) can be used to establish the softening point. The softening point is the temperature at which the DTA graph first exhibits a change of slope. While different polymer types ordinarily have different softening points, it will be appreciated that polymers of the same type, e.g., polypropylene, can have different softening points depending, for example, on molecular weight, etc.

When prepared as illustrated in FIG. 2, the pre-contact on the mat 12a with the heated roll 42 prior to the nip permits the fibers therein to soften to an extent such that, on compression in the nip, the microfibers in the mat regions in register with the raised points tend to flow around the continuous filaments thus not only achieving ply attachment but also aiding in integrating the continuous filaments into a coherent web. Autogenuous bonding is also achieved between the web filaments in those regions in register with the raised points. However, since the mat polymer aids in integrating the web, lower pressures can be used with the accompanying advantage that the physical structure of the continuous filaments is not adversely destroyed and the strength of the filaments thus preserved. The most appropriate bonding conditions for the preparation of a given material will depend on the particular components and can be determined with the benefit of the present description by simple experimentation. With respect to materials using polypropylene as the thermoplastic polymer for both the mat and web, roll temperatures on the order of about 270°-360° F., and preferably 290°-340° F., are useful (temperatures in lower portion of range being most useful with light weight materials) in combination with nip pressures (psi on raised points) of about 5,000-50,000, and, preferably, 6,000-15,000 (higher pressures in range being most useful with lower temperatures and heavy weight materials). Web speeds through the nip of about 100-300 feet per minute can be employed with the use of the higher speeds associated with the use of light weight web materials and high roll temperatures.

As will hereinafter be further discussed in connection with the Examples, materials with exceptionally improved strength characteristics can be obtained by accomplishing bonding in a manner such that highly uniform bonding is effected within the intermittent bond areas without a substantial degree of fusion of the continuous filaments occurring therein. When viewed under a polarizing microscope the filaments generally appear to be cohesively secured together at crossover points with their identification as individual filamentary indentities within the bond areas being possible. The microfibers appear to be substantially melted and fused within the bond area and in part encapsulate the continuous filaments. With respect to such materials wherein high pigment concentrations are not present in the thermoplastic polymers, the discrete bond areas have a uniform translucent appearance when held up to an ordinary artificial light source with substantially no portion of the individual areas being visably transparent.

Figure 3:
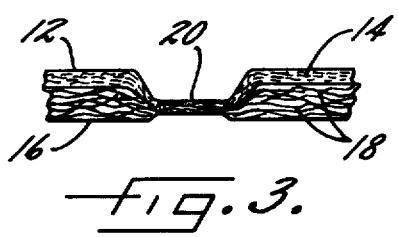
FIG. 3 is a sectional view looking along line 3—3 of FIG. 1.

Turning now to FIG. 3, there is schematically shown a cross section of a bond area of material prepared as illustrated in FIG. 2. The interesting thing to note with respect to this illustration is that the most predominent web depression due to passage through the nip is formed on the microfiber mat surface of the material and not on the continuous filament web surface which is in direct contact with the raised points. This phenomena is contrary to what is customarily observed with respect to passage of materials through nips such as illustrated and is believed to be due, at least in part, to the unique construction of the illustrated material. The importance of this feature is that, as ordinarily used, materials such as illustrated in FIG. 1 have the microfiber mat surface visably exposed. Having the three dimensional embossed like appearance illustrated in FIG. 3 is thus attractive. However, as previously discussed, in order to achieve adequate material strength it is desirable that the microfiber mat be adjacent the smooth surface roll 42 during bonding. Thus, as a result of the phenomena illustrated in FIG. 3, not only can desirable strength characteristics be achieved but, additionally, a textured microfiber mat surface can also be obtained.

Figure 4:
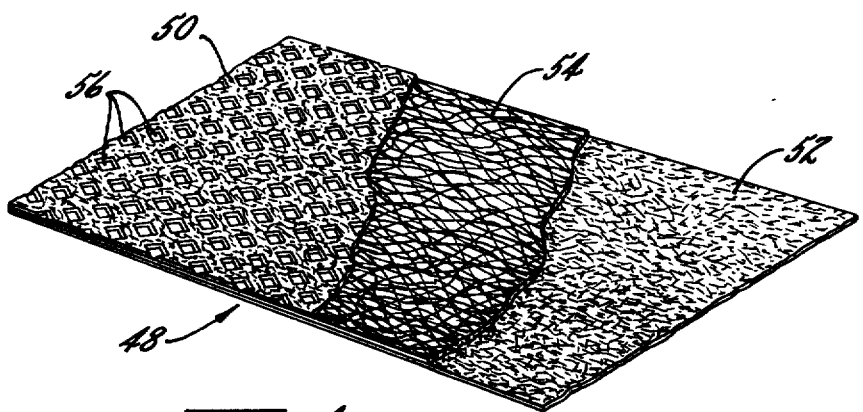
FIG. 4 is a fragmentary perspective view, with sections thereof broken away, of an additional embodiment of a material embodying the features of the present invention.

Turning now to FIG. 4, there is illustrated a further embodiment of the present invention wherein a material 48 is illustrated having, as outer plies, microfiber mats 50 and 52 and, as an inner ply a continuous filament web 54. Again, as illustrated in FIG. 1, ply attachment and integration of the continuous filament web is achieved by means of the regular pattern of intermittent bonds 56. As shown by the dotted lines in FIG. 2, preparation of a material such as depicted in FIG. 4 can be accomplished by combining a second microfiber mat 58 with the microfiber mat 12a and continuous filament web 16a at the nip formed by the rolls 34 and 36 ad thereafter passing the three ply composite through the roll 42. 44 bonding nip. Similarly, it will be understood that a microfiber mat can be formed on a wire such as 28 and thereafter continuous filament webs can be disposed on one or both sides of the mat to form other constructions embodying the features of the present invention.

The following Examples I-IV illustrate the preparation of nonwoven materials in accordance with the present invention. The results of measurements of certain physical properties of the materials so prepared and of their individual constituents are also reported. The results reported are averages of values obtained in the machine and cross directions. The measurements were made substantially in accordance with the following procedures:

| | |
|---|---|
| Strip Tensile | |
| Grab Tensile | ASTM-D-117-63 |
| Air Permeability | |
| Trapezoidal Tear | |
| Energy Absorption | Instron Corporation Manual Procedure No. 10-1-1c. |
| Water Repellency | 600 ml. of a normal saline solution are added to a one quart mason jar. A sample of the material to be tested is then placed over the mouth of the jar and the open ring screwed down on the jar tightly. The jar is then inverted on a glass plate located a few inches above a mirror. The repellency of the nonwoven material is measured as the time required for the first liquid water to penetrate the nonwoven material and wet the glass plate. |

Bonding was achieved using an arrangement such as illustrated in FIG. 2 wherein the rolls 42 and 44 were 6 inch diameter steel rolls. The raised points on the roll 44 were about 0.04 inch high and positioned such that the bonded material contained regularly spaced bonded areas in a diamond pattern in a density of about 214/in.$^2$. Each area was a square of about 0.03 inch on a side with a diagonal of the square positioned in the machine direction. About 17% of the surface area of the material was occupied by the bond areas. Rolls 40 and 46 were positioned such that 9 inches of wrap on the roll 42 surface was present prior to the bonding nip and 8 inches after the nip.

EXAMPLE I

| Material | |
|---|---|
| Layer of polypropylene microfiber mat (average fiber diameter about 6 microns, softening point about 137° C.)* | 0.45 oz./yd.$^2$ |
| Layer of polypropylene continuous filament web (average filament diameter about 18 microns softening point about 150° C.)* | 0.5 oz./yd.$^2$ |

*Same for all Examples reported herein unless otherwise specified

| Bonding Conditions | |
|---|---|
| Roll 42 | 273° F. |
| Roll 44 | 280° F. |
| Material Speed | 150 FPM |
| Pressure on raised points | 30,000 psi |

| Physical Properties | Strip Tensile (lbs/in) | % Elongation | Energy (in-lbs) | Grab Tensile (lbs.) | Trapezoid Tear (lbs) |
|---|---|---|---|---|---|
| Unbonded Microfiber Mat alone (.45 oz./yd.$^2$) | .8 | 47.6 | .84 | 2.0 | 0.5 |
| Bonded Microfiber Mat alone (.45 oz./yd.$^2$) | 1.4 | 26.2 | .45 | 1.6 | 0.3 |
| Bonded Continuous Filament Web alone (.5 oz./yd.$^2$) | 3.0 | 13 | .900 | 5.0 | 2.5 |
| Theoretical Laminated Material (based on sum of individual bonded components using highest microfiber mat values) | 4.4 | — | 1.74 | 7.0 | 3.0 |
| Example I laminated Material | 5.95 | 35 | 6.1 | 13.1 | 4.2 |

As is apparent from the above values, the laminated material prepared in accordance with Example I exhibits significantly higher strength characteristics than would be predicted from the strength characteristics of its individual constituents. The unexpected increase in strength is believed to be due to the manner in which the material is constructed and, in particular, the fact that the microfiber mat serves not only to achieve ply attachment but also aids in integrating the continuous filament web to provide reinforcement where filament attenuation and weakening may have occurred during the application of pressure. On visual examination of the material, the bond areas are seen to be substantially uniformly translucent in appearance. In addition to the illustrated desirable strength characteristics, the material possesses an overall opaque textile-like appearance, a desirable drape and full bodied hand, and is comfortable to the touch by appearing to equilibrate in moisture content with the surrounding atmosphere.

Furthermore, the material exhibits surprisingly good abrasion resistance in that the surfaces do not tend to get fuzzy or raise a pile during use. With respect to the continuous filament web side, the abrasion resistance obtained is believed to be attributable to the fact that the filaments are strongly held within the discrete bond areas without breakage thus avodiing the presence of long filament spans which would tend to "fuzz-up" during use. Insofar as the microfiber mat surface is concerned, the mat integrity achieved during formation is believed to aid in abrasion resistance as well as the fact that additional fiber bonding is effected during contact of the mat surface with the heated roll 42.

The material prepared as illustrated above is particularly suitable for applications where printing either for decorative or informative purposes is desired. It has been found that exceptional color fast printing can be accomplished on the microfiber mat surface of the material which not only has a high "bloom" as initially applied, but which remains sharp after exposure to the elements or repeated washing cycles. In this respect, it has been noted that these advantages are not achieved with respect to the continuous filament web alone. Furthermore, use of the material in fabric applications where repeated washing is anticipated is also highly desirable since the material appears to undergo less shrinkage on washing than does the continuous filament web as such.

In addition to the above mentioned desirable characteristics, the Example I material also possesses the combination of good water repellency and high air permeability. The average repellency of the material is about 44 minutes (hydrostatic head mason jar test) while the permeability is about 83 cubic feet per minute/ft.$^2$. This is to be contrasted with the microfiber mat itself which has substantially no water repellency and about 66 cubic feet per minute/ft.$^2$ permeability and the continuous filament web itself which while having high permeability has substantially no repellency. The combination of repellency and permeability exhibited by the Example I material renders it exceptionally suitable for fabric applications where a repellent, breathable material is required.

EXAMPLE II

Material

Same as Example I with addition of second 0.45 oz.-/yd.$^2$ polypropylene microfiber mat on other side of continuous filament web Bonding Conditions Same as Example I except at 160 FPM material speed Physical Properties

| | Strip Tensile (lbs/in) | % Elongation | Energy (in-lbs) | Grab Tensile (lbs) | Trapezoid Tear (lbs) |
|---|---|---|---|---|---|
| Theoretical Laminated | | | | | |

-continued

| | Strip Tensile (lbs/in) | % Elongation | Energy (in-lbs) | Grab Tensile (lbs) | Trapezoid Tear (lbs) |
|---|---|---|---|---|---|
| Material | 5.8 | — | 2.5 | 9 | 3.5 |
| Example II Laminated Material | 7.2 | 44.5 | 9.7 | 19.3 | 5.4 |

As illustrated, the material of Example II possesses the desirable strength characteristics discussed with respect to the Example I material as well as possessing the desirable textile-like characteristics heretofore identified. In addition, having the microfiber mat on both sides of the material permits either or both sides of the material to be printed with the accompanying advantages previously discussed.

EXAMPLE III

Material

Same as Example I with addition of second 0.5 oz./yd.$^2$ polypropylene continuous filament web on other side of microfiber mat Bonding Conditions Same as Example I except at 45,000 psi on raised points Physical Properties

| | Strip Tensile (lbs/in) | % Elongation | Energy (in-lbs) | Grab Tensile (lbs) | Trapezoid Tear (lbs) |
|---|---|---|---|---|---|
| Theoretical Laminated Material | 7.4 | — | 4.1 | 12 | 5.5 |
| Example III Laminated Material | 11.3 | 61 | 19.4 | 29.2 | 8.6 |

The Example III material exhibits a desirable uniform opaque appearance and has pleasing textile-like characteristics with respect to hand and drape. Furthermore, as illustrated, by including outer plies of the continuous filament web especially desirable strength characteristics can be achieved.

The material prepared in this Example again possesses many of the desirable characteristics identified previously with respect to Examples I–III. In addition, the Example IV material exhibits a very high water repellency (120 minutes) while exhibiting a permeability of 6.5 cubic feet per minute/ft.$^2$ rendering it suitable for many fabric applications.

A futher series of materials (Examples V–VII) were prepared in basically the same manner as the Example I–IV materials except that a fabric-wire pattern roll was used in place of the roll 44. The wire pattern simulated a plain weave pattern with elliptical shaped elements lying perpendicular to the machine direction and rectangular shaped elements lying parallel to the machine direction. The elements occupied an area of about 12% with a density of about 144/in.$^2$. The element height was approximately 0.14 inch at its highest point. Material bonding was accomplished at about 102 feet per minute with a pressure on the raised elements of about 5,500 psi. (calculated from loading on roll and area of elements). The smooth roll temperature was about 285° F. and pattern roll temperature about 290° F.

EXAMPLE V

| Materials | |
|---|---|
| Layer of polypropylene microfiber mat | 0.29 oz./yd.$^2$ |
| Layer of polypropylene continuous filament web | 0.56 oz./yd.$^2$ |

EXAMPLE IV

| Material | |
|---|---|
| Layer of polypropylene microfiber mat | 1.63 oz./yd.$^2$ |
| Layer of polypropylene continuous filament web | 0.5 oz./yd.$^2$ |
| Bonding Conditions | |
| Roll 42 | 273° F. |
| Roll 44 | 280° F. |
| Material Speed | 160 FPM |
| Pressure on raised points | 39,000psi |

| Physical Properties | Strip Tensile (lbs/in) | % Elongation | Energy (in-lbs) | Grab Tensile (lbs) | Trapezoid Tear (lbs) |
|---|---|---|---|---|---|
| Unbonded Microfiber Mat alond (1.63 oz./yd.$^2$) | 3.9 | — | 4.8 | 10.0 | 1.6 |
| Bonded Microfiber Mat alone* (1.63 oz./yd.$^2$) | 6.4 | 36.5 | 2.4 | 17 | 1.1 |
| Theoretical Laminated Material | 9.4 | — | 5.7 | 22 | 4.1 |
| Example IV Laminated Material | 7.3 | — | 7.5 | 29.4 | 5.3 |

*Pressure at 30,000 psi on raised points

-continued

| Physical Properties | Strip Tensile (lbs) | % Elongation | Energy (in-lbs) | Grab Tensile (lbs) | Trapezoid Tear (lbs) |
|---|---|---|---|---|---|
| Unbonded Microfiber Mat (.29 oz./yd.²) | .7 | — | .9 | 1.9 | .5 |
| Bonded Continuous Filament Web (.56 oz./yd.²) | 2.9 | 40 | 2.2 | 7.7 | 2.2 |
| Theoretical Laminated Material | 3.6 | — | 3.1 | 9.6 | 2.7 |
| Example V Laminated Material | 3.9 | — | 2.9 | 9.9 | 3.7 |

EXAMPLE VI

| Materials | | | | | |
|---|---|---|---|---|---|
| Layer of polypropylene microfiber mat | 0.59 oz./yd.² | | | | |
| Layer of polypropylene continuous filament web | 0.56 oz./yd.² | | | | |
| Physical Properties | Strip Tensile (lbs/in) | % Elongation | Energy (in-lbs) | Grab Tensile (lbs) | Trapezoid Tear (lbs) |
| Unbonded Microfiber Mat | 1.5 | — | 1.8 | 3.8 | 0.8 |
| Bonded Continuous Filament Web (.56 oz/yd.²) | 2.9 | 40 | 2.2 | 7.7 | 2.2 |
| Theoretical Laminated Material (based on sum of components) | 4.4 | — | 4.0 | 11.5 | 3.0 |
| Example VI Laminated Material | 4.4 | 33 | 3.4 | 14.1 | 4.5 |

EXAMPLE VII

| Material | | | | | |
|---|---|---|---|---|---|
| Layer of polypropylene microfiber mat | 0.88 oz./yd.² | | | | |
| Layer of polypropylene continuous filament web | 0.56 oz./yd.² | | | | |
| Physical Properties | Strip Tensile (lbs/in) | % Elongation | Energy (in-lbs) | Grab Tensile (lbs) | Trapezoid Tear (lbs) |
| Unbonded Microfiber Mat (0.88 oz./yd.² | 2.2 | — | 2.7 | 5.4 | 1.1 |
| Bonded Continuous Filament Web (0.56 oz./yd.²) | 2.9 | 40 | 2.2 | 7.7 | 2.2 |
| Theoretical Laminated Material | 5.1 | — | 4.9 | 13.1 | 3.3 |
| Example IV Laminated Material | 6.5 | 27 | 3.9 | 15.9 | 4.7 |

As is apparent from the reported physical properties, the values of the reported strength characterisitcs of the Example V-VII materials do not substantially exceed those theoretically predicted. In turn, on visual examination of the discrete bond areas in the material, it is noted that many of the individual areas are not uniformly translucent in appearance, when held up to a visible light source, there being a substantially transparent portion near the center of many of the areas which is either a perforation or a fused, film-like region. It is believed that the use of the described wire pattern wherein the height of the raised elements is not substantially the same over the surface of the individual elements results in excessively high pressures and accompanying overbonding within the bond regions thus preventing realization of exceptionally high strength properties. However, in other respects such as appearance, drape, printability and the like, the Example V-VII materials possess desirable characterisitcs.

In further keeping with the present invention, additional materials (Example VII-X) were prepared in a manner substantially similar to that described with respect to Examples I-IV except that the bonding rolls were larger and the bottom roll contained raised points occupying a total land area of about 24% in a density of about 200/in.² and a substantially uniform height of slightly less than 0.03 in. The construction of the materials, bonding conditions and physical properties of the resultant materials were as follows:

| Material | | | |
|---|---|---|---|
| Layer of polypropylene microfiber mat | 0.45 oz./yd.² | | |
| Layer of polypropylene continuous filament web | 1.4 oz./yd.² | | |
| Bonding Conditions | | | |
| Top Roll (° F.) | 330 | | |
| Bottom Roll (° F.) | 320 | | |
| Pressure (psi) | 16,500 | | |
| Speed (FPM) | 112 | | |
| Physical Properties | Grab Tensile Energy (in-lbs) | Grab Tensile (lbs.) | Trapezoid Tear (lbs.) |

| -continued | | | |
|---|---|---|---|
| Unbonded Microfiber Mat | 2.9 | 2.0 | 0.47 |
| Bonded Continuous Filament Web | 15.1 | 23 | 5.5 |
| Theoretical Laminated Material | 18.0 | 25 | 5.97 |
| Example VIII Laminated Material | 27.7 | 35.4 | 8.5 |

EXAMPLE IX

| Material | |
|---|---|
| Layer of polypropylene microfiber mat | 0.48 oz./yd.$^2$ * |
| Layer of polypropylene continuous filament web | 1.2 oz./yd.$^2$ ** |

\* mat alone bonded at 310° F. top roll, 300° F., bottom roll, 14,900 psi, and 200 FPM
\*\* web alone bonded at 330° F., top roll, 320° F., bottom roll, 16500 psi, and 68 FPM

| Bonding Conditions (except as specified above) | | | |
|---|---|---|---|
| Top Roll (° F.) | | | 330° F. |
| Bottom Roll (° F.) | | | 320° F. |
| Pressure (psi) | | | 14,900 psi |
| Speed (FPM) | | | 112 FPM |
| Physical Properties | Grab Tensile (lbs.) | Energy (in-lbs) | Trapezoid Tear (lbs.) |
| Unbonded microfiber Mat alone | 2.8 | 2.98 | .59 |
| Bonded microfiber Mat alone | 3.1 | 1.3 | .18 |
| Bonded Continuous Filament Web alone | 19.8 | 10.7 | 4.76 |
| Theoretical Laminated Material | 22.9 | 13.6 | 5.3 |
| Example IX Laminated Material | 33.6 | 25.4 | 7.4 |

EXAMPLE X

| Material | | | |
|---|---|---|---|
| Layer of polypropylene microfiber mat | | | 0.3 oz./yd.$^2$ |
| Layer of polypropylene continuous filament web | | | .49 oz./yd.$^2$ |
| Bonding Conditions | | | |
| Top Roll (° F.) | | | 287° F. |
| Bottom Roll (° F.) | | | 290° F. |
| Pressure (psi) | | | 11,000 psi |
| Speed (FPM) | | | 300 FPM |
| Physical Properties | Grab Tensile (lbs.) | Energy (in-lbs.) | Trapezoid Tear (lbs.) |
| Unbonded Microfiber Mat alone | 1.9 | — | .5 |
| Bonded Continuous Filament Web alone | 5.1 | 2.4 | 1.75 |
| Theoretical Laminated Material | 7.0 | — | 2.2 |
| Example X Laminated Material | 11.5 | 7.5 | 2.4 |

The Example VIII X materials possess many of the desirable attributes heretofore identified with respect to other materials prepared in accordance with the present invention and particularly unexpectedly high strength characteristics. In addition, these materials were found to exhibit a marked two-sidedness when saturated with liquid. The liquid tended to concentrate in the microfiber mat layer leaving the continuous filament web side relatively dry. Thus, the material is a cloth-like sheet, which, when saturated with water and wrung out, functions effectively as a wet wash cloth on one side and a semi-dry towel on the other. This behavior is believed to be characterisitc of materials constructed in accordance with the present invention wherein the continuous filament web is present in about 60-80% by weight with the microfiber mat being present in about 20-40% by weight. Such materials are believed to be particularly useful as wipes for adding or removing water, polishes, and solvents and the like as well as for portable prewetted wash cloths for personnal use.

Several additional materials (Examples XI and XII) were prepared using the fabric-wire pattern roll described with respect to Examples V–VII and a nylon 6, polypropylene polymer mixture for the preparation of the microfibers of the mat. The materials so prepared were of the following construction:

EXAMPLE XI

| Material | |
|---|---|
| Layer of Microfiber Mat (50% by weight nylon 6, 50% by weight polypropylene) | 0.5 oz./yd.$^2$ |
| Layer of Polypropylene Continuous Filament Web | 1.25 oz./yd.$^2$ |

EXAMPLE XII

| Material | |
|---|---|
| Layer of Microfiber Mat (25% by weight nylon 6, 75% by weight polypropylene) | 0.4 oz./yd.$^2$ |
| Layer of Polypropylene Continuous Filament Web | 1.3 oz./yd.$^2$ |

The bonding conditions were as follows:

| | Example XI | Example XII |
|---|---|---|
| Top Roll (° F) | 290 | 320 |
| Bottom Roll (° F) | 295 | 315 |
| Pressure (psi) | 7200 | 6800 |
| Speed (FPM) | 45 | 85 |

The materials had the following physical properites:

|  | Grab Tensile (Lbs.) | Trapezoid Tear (Lbs.) |
| --- | --- | --- |
| For Example XI |  |  |
| Theoretical | 26.7 | 5.9 |
| Actual | 24.5 | 7.5 |
| For Example XII |  |  |
| Theoretical | 26.6 | 6.8 |
| Actual | 30.5 | 8.3 |

These materials possess many of the desirable attributes heretofore identified which are representative of materials emboyding the features of the present invention. In addition, the nylon constituent in the microfibers presents reactive sites for chemical bonding with surface finishing reagents such as dyes and the like which are normally non-reactive with polypropylene fibers.

In accordance with a specific aspect of this invention, it has been found that certain laminates as herein described are exceptionally useful as sterile wrappers or containment fabrics for surgical and other health care procedures. As is well recognized, fabrics useful for these purposes must permit penetration of a sterilent (ethylene oxide at about 130° F., steam at about 250°-280° F., gamma radiation, etc.), thereafter impeded to a high degree passage of bacteria and like contaminants, be anti-static and preferably also fluid repellent.

The laminates illustrated herein which are especially useful for such applications generally have a basis weight of about 0.8-2 oz./yd.$^2$ and contain at least about 0.3 oz./yd.$^2$ of the microfiber mat and at least about 0.5 oz./yd.$^2$ of the continuous filament web. The higher basis weight materials (1.5 oz./yd.$^2$-2 oz./yd.$^2$) are useful in wrapper applications such as for sterile gloves, syringes, etc., where some degree of stiffness to permit sealing, ease in storage and subsequent dispensing is desirable. Lower basis weight materials (0.8 oz./yd.$^2$-1.5 oz./yd.$^2$ and preferably above 1.1 oz./yd.$^2$) are most useful where drapability, quietness and the like are especially important. These applications include, among other, wraps for surgical instruments and packs, surgical caps, gowns and patient drapes, surgical table and Mayo stand covers, isolation gowns and scrub apparel.

In selecting the ratio of microfiber mat to continuous filament web, lower ratios are associated with uses where greater strength characteristics and less stringent barrier properties are required. As the microfiber mat content of the laminate is increased better barrier characteristics are noted but permeability is diminished. Preferred laminates are those wherein the mat to web ratio is less than about 1:1 (e.g., 7:1 to 0.9:1) and the fibers of the microfiber mat have an average diameter of about 6 microns.

After preparation, it is necessary to treat the laminates with an antistatic composition in order to reduce surface resistivity to below about $1 \times 10^{12}$ ohms/square and usually to less than $1 \times 10^{11}$ ohms/square (AATCC Text Method 76:1972). Any number of antistatic compositions can be used for this purpose with the general requirements, in addition to reducing resistivity, being that the composition is non-toxic, does not promote bacterial growth, does not adversely affect sterilent penetration or barrier properties and, if steam sterilization is anticipated, be durable. Many useful compositions are disclosed in "Antistatic Agents, Technology and Applications 1972", Keith Johnson, Noyes Data Corporation, with polymeric amines and salts thereof being particularly useful.

Since many antistatic compositions also exhibit wetting characteristics which can adversely affect fluid repellency, both with respect to water and alcohol, it is frequently desirable to treat the material with a fluid repellent composition in order to avoid moisture transmitted contamination. Also, by providing alcohol repellency the fabric, when used as a sterile wrapper, can be marked, such as with a customary felt pen, to identify the wrapped items. Suitable treating materials such as fluorocarbons which are useful in obtaining fluid repellency are well known and commercially available.

An especially useful technique for measuring water repellency of treated materials is standard AATCC Test Method 42-1972. The degree of repellency by this method is indicated by the quantity of water which, on impact, penetrates the material being tested. 500 grams of water are originally used and the results are reported in grams of water which penetrates the material with lower values associated with greater repellency. While very low values, e.g., less than about 2-3 grams, are preferred, materials having impact repellency values of less than about 30 grams and especially less than about 20 grams are generally useful

EXAMPLE XIII

A laminate was prepared generally in accordance with the Example I procedure containing about 0.6 oz./yd.$^2$ of microfiber mat and about 0.8 oz./yd.$^2$ of continuous filament web. An antistatic composition was then applied to the laminate by passing it (at 175 fpm) through a bath containing the following ingredients in parts by weight.

| | |
| --- | --- |
| Water | 789 |
| "ZELEC" DP antistat (DuPont-quaternary ammonium salt aqueous emulsion) | 1 |
| FC-808 fluid repellent (3M Company --high molecular weight cationic fluorocarbon aqueous emulsion) | 8 |
| Medical Antifoam C (Dow) | .8 |
| Synthrapol KB (ICI) wetting agent | 1.9 |

The material was then dried by passage over hot cans. The resulting material contained, by weight, 0.1% of "ZELEC" DP and 0.2% of FC-808. The presence of the antistatic composition reduced the surface resistivity of the laminate of about $10^{15}$ ohms/square to about $10^9$ ohms/square. The reduced level of resistivity was retained after subsequent sterilization (both steam and ethylene oxide) which was readily effected in conventional fashion. The sterilized material had desirable characteristics of water and alcohol repellency and, in addition, exhibited particularly advantageous bacterial barrier properties.

As has been illustrated, nonwoven materials are provided by the present invention which fully satisfy the aims and objectives initially set forth. Materials are provided which are fabric-like in drape, hand, and appearance. By employing the techniques illustrated herein, breathable, fluid repellent materials can be fashioned which are highly suitable for garment applications such as outwear lining, jackets, rainwear and the like. Furthermore, it has been found that those materials herein illustrated which have, as an exposed surface, a microfiber mat can be advantageously printed to provide decorative fabrics and, in addition, possess fluid retentive characteristics rendering them suitable as wipes as well as receptive to treatment with wetting agents and the like to impart absorbency characteristics.

Moreover, it has been illustrated that by appropriate bonding, nonwoven materials of the present invention can be fashioned with particularly outstanding strength characteristics. In particular, as shown by Examples I-IV, materials can be prepared with particularly enhanced energy absorbing characteristics, the improvement in energy absorption over that theoretically predicted being on the order of at least about 25% and frequently in excess of 100%. The importance of high energy absorption resides in the fact that energy absorption is indicative of the ability of the material to deform under strain without catastrophic rupture. A high capacity for absorbing energy means that the material possesses a continued load bearing ability as it is strained and is particularly important in applications such as garments and sheets where, in use, the material is constantly subjected to strains at localized areas such as the toe area in bed sheets and the elbow and knee areas in wearing apparel. Such uses may include: robe linings and facings; mattress pads, covers and ticking; shower curtains, drapes and drapery liners; pillow ticks, protectors and pillowcases; bedspreads and quilts; and, sleeping and slumber bags and liners. Similarly, with respect to the other strength characteristics, particularly grab tensile and trapezoid tear, a similar unexpected improvement in strength can be achieved which, as illustrated, is generally on the order of at least about 30% and generally at least about 50% compared with that theoretically predicted.

Lastly, there have been described herein materials which, when appropriately treated, are useful as sterilizable fabrics for hospital and health care applications.

We claim as our invention:

1. A nonwoven fabric-like material comprising a web of substantially continuous and randomly deposited, molecularly oriented filaments of a thermoplastic polymer having an average filament diameter in excess of about 12 microns and an integrated mat of generally discontinuous, thermoplastic polymeric microfibers having an average fiber diameter of up to about 10 microns and a softening temperature of about 10°-40°C. less than the softening temperature of the continuous filaments; said web and mat being positioned in laminar surface-to-surface relationship and united together at intermittent discrete bond regions formed by the application of heat and pressure to thereby provide a unitary structure having desirable textile-like appearance and drape characteristics and to integrate the web of substantially continuous filaments so that said web can function as an effective load bearing constituent of the material during straining thereof.

2. The nonwoven fabric-like material of claim 1 wherein the discrete bond regions are present in a density of about 50-1,000/in.$^2$ and occupy about 5-50% of the surface area of the material.

3. The nonwoven fabric-like material of claim 1 wherein the discrete bond regions are present in a density of about 100-500/in.$^2$ and occupy about 10-30% of the surface area of the material.

4. The nonwoven fabric-like material of claim 3 wherein the intermittent discrete bond regions are uniformly bonded without a substantial degree of fusion of the continuous filament occurring therein.

5. The nonwoven fabric-like material of claim 4 having a basis weight of up to about 4 oz./yd.$^2$.

6. The nonwoven fabric-like material of claim 5 wherein the average filament diameter of the filaments of the continuous filament web is about 12-55 microns.

7. The nonwoven fabric-like material of claim 6 wherein the average filament diameter of the filaments of the continuous filament web is about 15-25 microns.

8. The nonwoven fabric-like material of claim 7 wherein the ratio of the mat to the web is about 0.2:1 to 4:1 by weight.

9. The nonwoven fabric-like material of claim 8 having a basis weight of about 0.75-2.5 oz./yd.$^2$.

10. The nonwoven fabric-like material of claim 9 wherein the thermoplastic polymer filaments and the thermoplastic polymeric microfibers are of polypropylene.

11. The nonwoven fabric-like material of claim 1 wherein a second polymeric microfiber mat is united to the web on the other surface thereof to provide a material which is highly suitable for decorative or informative printing.

12. A sterile wrap for wrapping about items to be sterilized for subsequent use in surgical procedures, said sterile wrap having a surface resistivity of less than $1 \times 10^{12}$ ohms/square and comprising a web, having a basis weight of at least about 0.5 oz./yd.$^2$ of substantially continuous and randomly deposited, molecularly oriented filaments of a thermoplastic polymer having an average filament diameter in excess of about 12 microns and, to provide bacterial barrier properties and yet allow sterilant penetration, an integrated mat, having a basis weight of at least about 0.3 oz.yd.$^2$, of generally discontinuous, thermoplastic polymeric microfibers having an average fiber diameter of up to about 10 microns, said web and mat being positioned in laminar surface-to-surface relationship and united together at intermittent discrete bond regions formed by the application of heat and pressure to thereby provide a unitary structure having a desirable textile-like appearance and drape characteristics and to integrate the web of substantially continuous filaments and the microfiber mat so that said web can function as an effective load bearing constituent of the material while said mat retains said sterilant penetration and bacterial barrier properties in said material.

13. The sterile wrap of claim 12 wherein the thermoplastic polymer filaments and the thermoplastic polymeric microfibers are of polypropylene.

14. The sterile wrap of claim 13 having a basis weight of about 0.8 oz./yd.$^2$-2 oz./yd.$^2$.

15. The sterile wrap of claim 14 having a surface resistivity of less than $1 \times 10^{11}$ ohms/square.

16. The sterile wrap of claim 15 wherein the ratio of the mat to the web is less than about 1:1 by weight.

17. The sterile wrap of claim 16 wherein the ratio of the mat to the web is about 0.7:1-0.9:1 by weight.

18. The sterile wrap of claim 17 having a basis weight of about 1.1-1.5 oz./yd.$^2$.

19. The sterile wrap of claim 12 wherein a second web having a basis weight of at least about 0.5 oz./yd.$^2$ of substantially continuous and randomly deposited, molecularly oriented filaments of a thermoplastic polymer is united to the mat on the other surface thereof.

20. The sterile wrap of claim 12 wherein the discrete bond regions are present in a density of about 50-1,000/in.$^2$ and occupy about 5-50% of the surface area of the material.

21. The sterile wrap of claim 12 wherein the discrete bond regions are present in a density of about 100-500-

/in.² and occupy about 10–30% of the surface area of the material.

22. the sterile wrap of claim 21 wherein the intermittent discrete bond regions are uniformly bonded without a substantial degree of fusion of the continuous filaments occurring therein.

23. The sterile wrap of claim 12 wherein the average filament diameter of the filaments of the continuous filament web is about 12–55 microns.

24. The sterile wrap of claim 24 wherein the average filament diameter of the filaments of the continuous filament web is about 15–25 microns.

25. The sterile wrap of claim 12 wherein a second polymeric microfiber mat is united to the web on the other surface thereof to provide a material which is highly suitable for decorative or informative printing.

26. The nonwoven fabric-like material of claim 1 wherein a second web of substantially continuous and randomly deposited, molecularly oriented filaments of a thermoplastic polymer is united to the mat on the other surface thereof.

* * * * *